(12) United States Patent
Kronstedt et al.

(10) Patent No.: US 10,398,335 B2
(45) Date of Patent: Sep. 3, 2019

(54) BRIDGE CONNECTORS EMPLOYING FLEXIBLE PLANAR BODIES HAVING SIGNAL PATHWAYS COUPLING CONTROL DEVICES WITH BIOMETRIC SENSORS

(71) Applicant: Preventice Technologies, Inc., Rochester, MN (US)

(72) Inventors: Brian Walter Kronstedt, Shoreview, MN (US); Scott J. Burrichter, Rochester, MN (US); Andrew Arroyo, Austin, TX (US)

(73) Assignee: Preventice Technologies, Inc., Rochester, MN (US)

( * ) Notice: Subject to any disclaimer, the term of this patent is extended or adjusted under 35 U.S.C. 154(b) by 871 days.

(21) Appl. No.: 14/819,012

(22) Filed: Aug. 5, 2015

(65) Prior Publication Data

US 2017/0035314 A1  Feb. 9, 2017

(51) Int. Cl.
*A61B 5/0416* (2006.01)
*A61B 5/0408* (2006.01)

(52) U.S. Cl.
CPC ........ *A61B 5/0416* (2013.01); *A61B 5/04085* (2013.01); *A61B 2562/164* (2013.01); *A61B 2562/22* (2013.01); *A61B 2562/227* (2013.01)

(58) Field of Classification Search
CPC .......... A61B 5/04085; A61B 2562/164; A61B 2562/228; A61B 2562/227
See application file for complete search history.

(56) References Cited

U.S. PATENT DOCUMENTS

| 3,868,946 A | | 3/1975 | Hurley | |
|---|---|---|---|---|
| 5,479,934 A | * | 1/1996 | Imran | A61B 5/0017 600/390 |
| 5,928,142 A | * | 7/1999 | Cartmell | A61B 5/04087 600/372 |
| 6,076,003 A | * | 6/2000 | Rogel | A61B 5/04085 600/390 |
| 6,117,077 A | * | 9/2000 | Del Mar | A61B 5/04085 600/300 |
| 6,161,036 A | * | 12/2000 | Matsumura | A61B 5/0006 128/903 |

(Continued)

*Primary Examiner* — Lee S Cohen
*Assistant Examiner* — Erin M Cardinal
(74) *Attorney, Agent, or Firm* — Patterson + Sheridan, LLP

(57) ABSTRACT

Bridge connectors employing flexible planar bodies having signal pathways coupling control devices with biometric sensors are disclosed. Sensors are placed in contact with a patient to detect a health condition and generate an output signal based on the health condition. A control device is linked to the sensors to receive the output signal for collection, analysis, storage, display, and/or subsequent transfer. A bridge connector includes a planar body with predetermined flexibility and signal pathways extending between data ports. By removably coupling the bridge connector to the control device and the sensors secured to the patient, the control device may be physically supported by the patient with minimal discomfort and low-cost biometric sensors may be used. In this manner, sensor replacement costs are reduced and the useful lives of the sensors can be maximized as the designed flexibility of the bridge connector facilitates removable coupling with the biometric sensors.

20 Claims, 9 Drawing Sheets

(56) References Cited

U.S. PATENT DOCUMENTS

| | | | |
|---|---|---|---|
| 6,259,939 B1* | 7/2001 | Rogel | A61B 5/04085 128/903 |
| 6,453,186 B1 | 9/2002 | Lovejoy et al. | |
| 6,605,046 B1* | 8/2003 | Del Mar | A61B 5/04085 600/507 |
| 7,616,980 B2 | 11/2009 | Meyer | |
| 8,690,611 B2 | 4/2014 | Selvitelli et al. | |
| 2003/0171798 A1* | 9/2003 | Nova | A61N 1/04 607/142 |
| 2004/0077954 A1* | 4/2004 | Oakley | A61B 5/0006 600/483 |
| 2005/0054941 A1* | 3/2005 | Ting | A61B 5/0408 600/529 |
| 2007/0270678 A1* | 11/2007 | Fadem | A61B 5/0006 600/372 |
| 2008/0139953 A1* | 6/2008 | Baker | A61B 5/0006 600/509 |
| 2008/0288026 A1* | 11/2008 | Cross | A61B 5/0408 607/60 |
| 2008/0312520 A1* | 12/2008 | Rowlandson | A61N 1/048 600/372 |
| 2009/0105577 A1* | 4/2009 | Wu | A61B 5/0478 600/383 |
| 2010/0042012 A1* | 2/2010 | Alhussiny | A61B 5/04085 600/546 |
| 2010/0228113 A1* | 9/2010 | Solosko | A61B 5/0416 600/382 |
| 2010/0234715 A1* | 9/2010 | Shin | A61B 5/0402 600/388 |
| 2010/0256475 A1* | 10/2010 | Chiang | A61B 5/04 600/388 |
| 2012/0246795 A1* | 10/2012 | Scheffler | A41D 1/002 2/69 |
| 2012/0323098 A1* | 12/2012 | Moein | A61B 5/6848 600/345 |
| 2013/0019383 A1* | 1/2013 | Korkala | A61B 5/6804 2/338 |
| 2013/0225966 A1* | 8/2013 | Macia Barber | A61B 5/04085 600/388 |
| 2014/0187899 A1* | 7/2014 | Pernu | A61B 5/0416 600/388 |
| 2015/0094558 A1* | 4/2015 | Russell | A61B 5/688 600/391 |

* cited by examiner

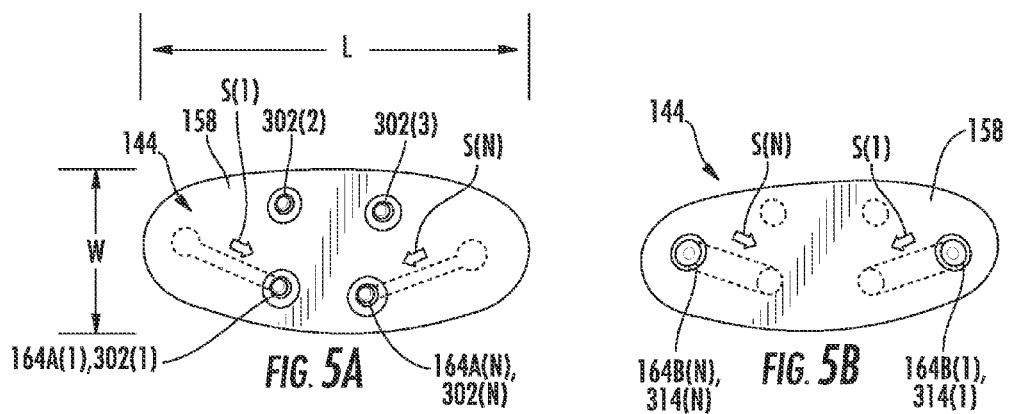
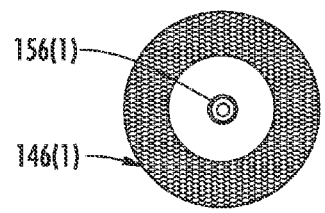
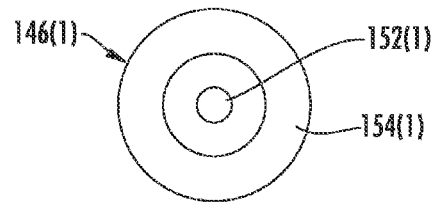

BRIDGE CONNECTORS EMPLOYING FLEXIBLE PLANAR BODIES HAVING SIGNAL PATHWAYS COUPLING CONTROL DEVICES WITH BIOMETRIC SENSORS

BACKGROUND

Field

The present disclosure relates to patient healthcare systems, and in particular, to connectors coupling control devices with biometric sensors (e.g., electrocardiogram electrodes).

Description of the Related Art

Through advances in information technology, modern healthcare providers can quickly and easily visualize health conditions and vital statistics for a patient. For instance, biometric sensors may detect at least one health condition including a vital statistic of a patient and generate a signal including data based on the condition. For example, biometric sensors could be used to detect health conditions in the form of heart rate data, electrocardiogram data, blood pressure data, blood sugar data, and so on for a patient. These conditions may be collected over time and presented to health care providers caring for the patient. For example, a health care provider could monitor health conditions for the patient over extended timeframes, e.g., twenty-four hours or more, to monitor the health of the patient and to identify abnormalities which may occur. The abnormalities may be observable as changes in the biometric data. The abnormalities may be used by the medical care provider to provide long term care to the patient, predict future medical events, or to diagnose medical conditions of the patient.

Biometric sensors or other measurement instruments may be directly attached to a patient's skin to detect health conditions and generate signals including data based on the health condition. The specific positions where health conditions may be detected are predetermined according to the health condition monitored and the location at the patient where the detection may practically occur. The signals generated by the biometric sensors can be communicated to a control device, which may then collect, analyze, transmit, display, and/or store the signals or alerts derived therefrom. In mobile or long-term use situations, the control device and the biometric sensor are conventionally provided in two parts: the control device and a customized, wearable patch that includes the biometric sensors and an interface to provide connectivity from the skin of the patient to the control device. The patch may, for example, be worn by the patient for several days during the time period of a medical prescription. Typically, these patches are disposable and have a limited useful life as patients often discard these patches after two to seven days of use, e.g., due to diminished contact of the biometric sensors of the patch with the skin of the patient.

There are several issues that have sometimes arisen with the use of conventional patches. For example, conventional patches can suffer from reduced or limited life of the electrodes because of limitations of the skin-contacting bonding agent. Also, some patients may experience discomfort with the patch and consequently scratch, pull at, or altogether remove the patch from the skin. These patches often include relatively expensive conductive materials (e.g., silver/silver chloride) which extend from the biometric sensors to form connective interfaces with the control device, resulting in an increased cost for the device offering. As such, new lower cost approaches are needed to enable the biometric sensors to be worn by the patient for as long as possible with minimal discomfort and maintain contact with the skin of the patient to obtain accurate data of the health condition.

SUMMARY

Bridge connectors employing flexible planar bodies having signal pathways coupling control devices with biometric sensors are disclosed. Biometric sensors are placed in contact with a patient to detect a health condition and generate an output signal based on the health condition. A control device is linked to the sensors to receive the output signal for collection, analysis, storage, display, and/or subsequent transfer. A bridge connector includes a planar body with predetermined flexibility and signal pathways extending between data ports. By removably coupling the bridge connector to the control device and the sensors secured to the patient, the control device may be physically supported by the patient with minimal discomfort and low-cost biometric sensors may be used. In this manner, sensor replacement costs are reduced and the useful lives of the sensors can be maximized as the designed flexibility of the bridge connector facilitates removable coupling with the biometric sensors.

One embodiment provides a bridge connector for coupling a control device to at least one biometric sensor. The bridge connector includes a flexible planar body including a first surface and a second surface opposite the first surface. The first and second surfaces are separated by a thickness of the flexible planar body. The flexible planar body including at least one signal pathway interconnecting data ports at the first and the second surfaces according to a predetermined relationship. The data ports at the first surface are configured to be removably coupled to the control device. The data ports at the second surface are configured to be removably coupled to the at least one biometric sensor, and the data ports are configured to exchange biometric data between the data ports through the at least one signal pathway and according to the predetermined relationship. In this manner, the cost can be reduced as the bridge connectors may be reused as the biometric sensors are exchanged and discarded.

In another embodiment, a method of receiving biometric data from a patient is disclosed. The method includes positioning at least one biometric sensor relative to a patient. The method also includes removably coupling data ports at a first surface of a flexible planar body of a bridge connector to device data ports on a control device. The method also includes removably coupling data ports at a second surface of the flexible planar body of the bridge connector to the at least one biometric sensor. The second surface is opposite the first surface, and the first and second surfaces are separated by a thickness of the flexible planar body. The method also includes generating, with the at least one biometric sensor, an output signal including biometric data measured by the at least one biometric sensor from the patient. The method also includes receiving the output signal at the device ports of the control device through at least one signal pathway of the flexible planar body, wherein the at least one signal pathway interconnects data ports at the first and the second surfaces according to a predetermined relationship. In this manner, in case the bridge connector or any of the at least one biometric sensor becomes inoperable, then either may be replaced without the needing to discard both the bridge connector and the at least one biometric sensor.

A medical device for receiving biometric data from a patient is also disclosed. The medical device includes at least one biometric sensor for measuring biometric data of a patient and configured to generate at least one output signal including the biometric data. The medical device further includes a control device for receiving the output signal. The medical device further includes a bridge connector for coupling the control device to at least one biometric sensor. The control device includes a flexible planar body including a first surface and a second surface opposite the first surface. The first and second surfaces are separated by a thickness of the flexible planar body. The flexible planar body including at least one signal pathway interconnecting data ports at the first and the second surfaces according to a predetermined relationship. The data ports at the first surface are configured to be removably coupled to the control device. The data ports at the second surface are configured to be removably coupled to the at least one biometric sensor, and at least one signal pathway is configured to exchange biometric data between the data ports according to the predetermined relationship. In this manner, biometric data can be more efficiently received from the patient as more expensive materials used in the biometric sensors can be practically avoided in the manufacture of the bridge connector.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 5A and 5B are a top view and a bottom view, respectively, of the bridge connector of FIG. 1, according to one embodiment described herein.

FIGS. 6A and 6B are a top view and a bottom view, respectively, of one of the biometric sensors of FIG. 1, according to one embodiment described herein.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Control devices provide opportunities for a care provider (e.g., a physician, nurse, technician, etc.) to improve patient care. An event manager can utilize data provided by control devices or an "internet of things" (IoT) device to identify health events that range from identifying critical health care issues such as cardiac or respiratory emergencies to maintenance events where the control device fails, e.g., because a battery is low or a wire is disconnected. To process health related events, the control device may be physically supported by the patient, biometric sensors, and a bridge connector in a predefined position relative to the patient. In this predefined position the biometric sensors are in contact with, and secured to, the patient to form a foundation from which the bridge connector and the control device can be supported. Further, in this predefined position the biometric sensors can be coupled to the bridge connector to measure a health condition of the patient and generate an output signal. The output signal includes information regarding a health condition of the patient. The bridge connector includes signal pathways linking the control device to the biometric sensors, so that the control device may receive the output signal. The bridge connector also includes a flexible planar body with predetermined structural rigidity to conform to a shape of the patient and provide a relatively uniform contact between the biometric sensors and the patient, so that patient comfort is improved and biometric sensor life is maximized between sensor replacements. The bridge connector may be configured to be removably coupled to the biometric sensors to enable standard biometric sensors to be used and enable the bridge connector to be reused thereby reducing hardware expenses after biometric sensors are replaced.

Figure 1:
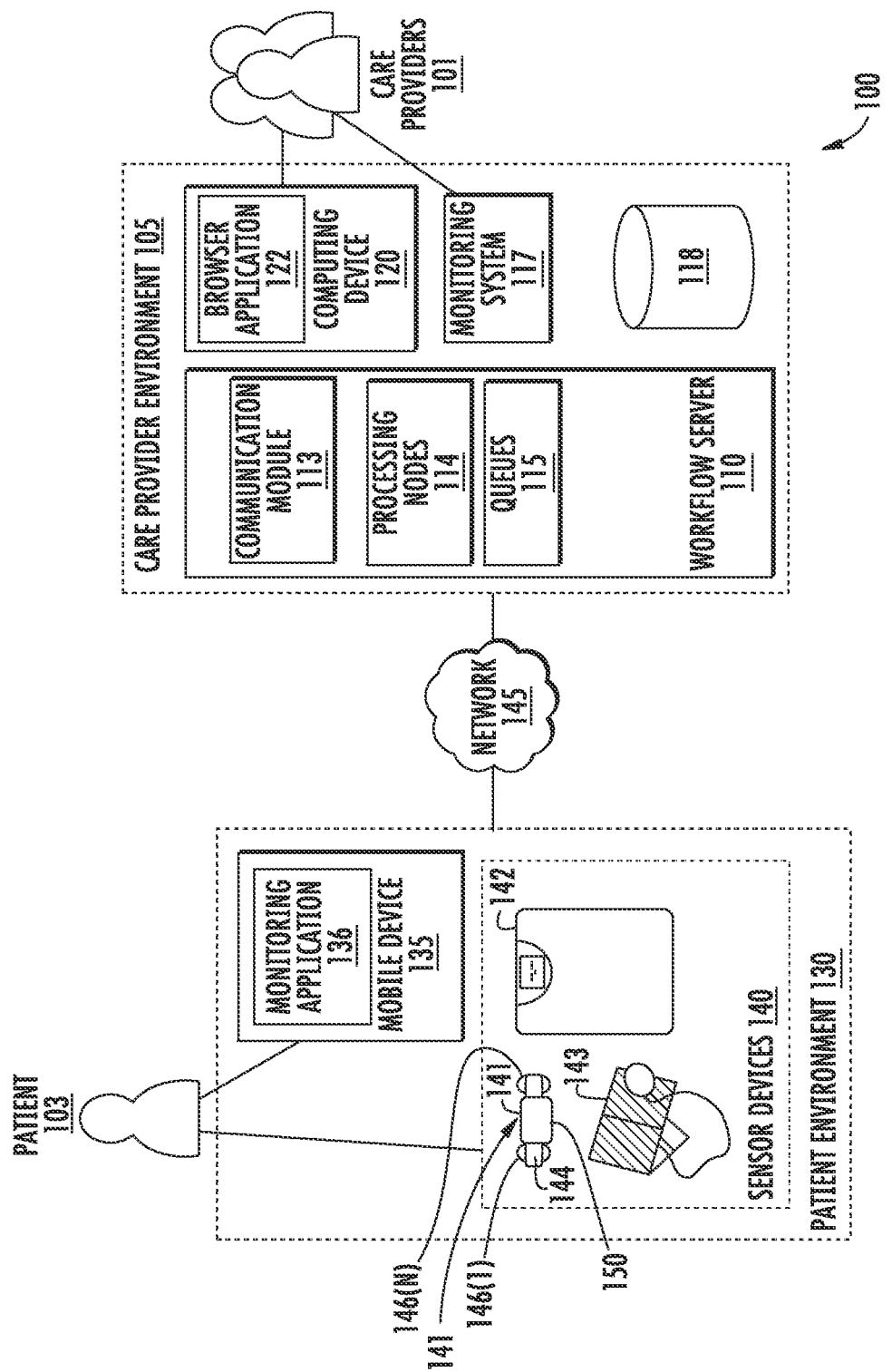
FIG. 1 illustrates an example computing environment, according to one embodiment comprising an exemplary control device, bridge connector, and at least one biometric sensor in the context of a patient, according to one embodiment described herein.

In this regard, FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data collected from the patient 103 in the patient environment 130.

The care provider environment 105 may include a workflow server 110, a computing device 120, monitoring system 117 and data repository 118. Each of the workflow server 110, the computing device 120, and the monitoring system 117 may be a physical computing system that includes one or more computing devices 120 or a virtual computer instance (e.g., executing in a cloud computing platform). A care provider 101 may use the computing device 120 to access (e.g., via a browser application 122, a native application on the computing devices 120, etc.) a user interface (UI) hosted by the monitoring system 117.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated a biometric sensor has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if he or she has any symptoms or instructing the patient 103 to reattach a disconnected biometric sensor 146(1) (FIG. 2B) of the at least one sensor device 140.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a health event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and/or a blood pressure cuff 143. Each of the at least one sensor device 140 may capture different vitals of the patient 103. For example, when applied to a body of patient 103, the body sensor 141 captures real-time biometric data (e.g., heart rate, ECG data, etc.). In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that electrocardiogram (ECG) data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

With continued reference to FIG. 1, the body sensor 141 may collect, analyze, store, and/or transmit a signal indicating a health condition of the patient 103 to the mobile device 135 and/or the care provider environment 105 through the network 145. The body sensor 141 includes a control device 150, a bridge connector 144, and at least one biometric sensor 146(1)-146(N). The control device 150 communicates with the biometric sensors 146(1)-146(N) through the bridge connector 144. The biometric sensors 146(1)-146(N) contact the patient 103 and respectively generate at least one output signal S(1)-S(N) (see FIG. 2B) indicating a health condition of the patient 103. The output signals S(1)-S(N) are received by the control device 150 by use of the bridge connector 144 which also physically supports the control device 150. In this manner, the control device 150 receives the output signals S(1)-S(N) from the biometric sensors 146(1)-146(N).

Figure 2A:
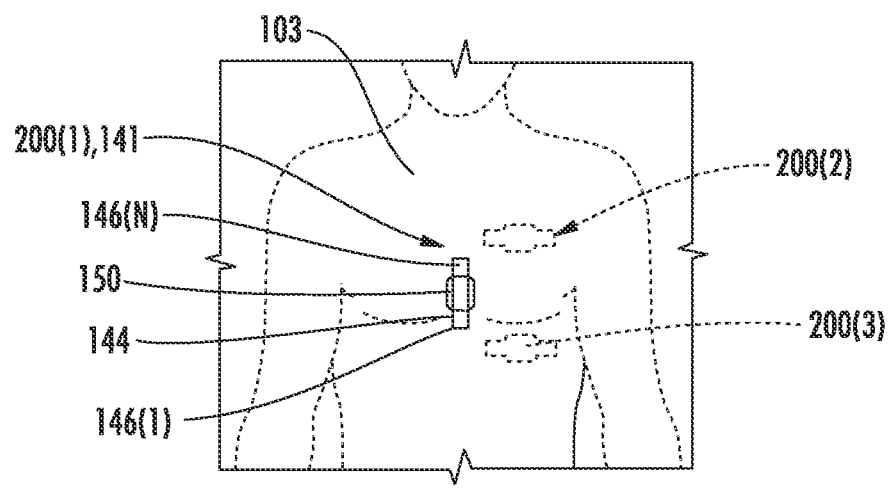
FIG. 2A is an anterior view of the patient with the control device, the bridge connector, and the at least one biometric sensor of FIG. 1 positioned relative to the patient in various exemplary positions to measure biometric information from the patient, according to one embodiment described herein.

FIG. 2A is an anterior view of the patient 103 with the body sensor 141 including the control device 150, the bridge connector 144, and the biometric sensors 146(1)-146(N) of FIG. 1 positioned relative to the patient 103 in various exemplary locations 200(1)-200(3) to measure biometric information from the patient 103. The locations 200(1)-200(3) may be predetermined to locate the biometric sensors 146(1)-146(N) proximate to physical sources of biometric data to be measured and that are indicative of a health condition of the patient, e.g., the electrical activity of the heart of the patient 103 over time. In this manner, the biometric sensors 146(1)-146(N) may generate the output signals S(1)-S(N) indicating a health condition of the patient 103 which when received by the control device 150 could be collected, analyzed, stored and/or transmitted to the mobile device 135 and/or network 145.

Figure 2B:
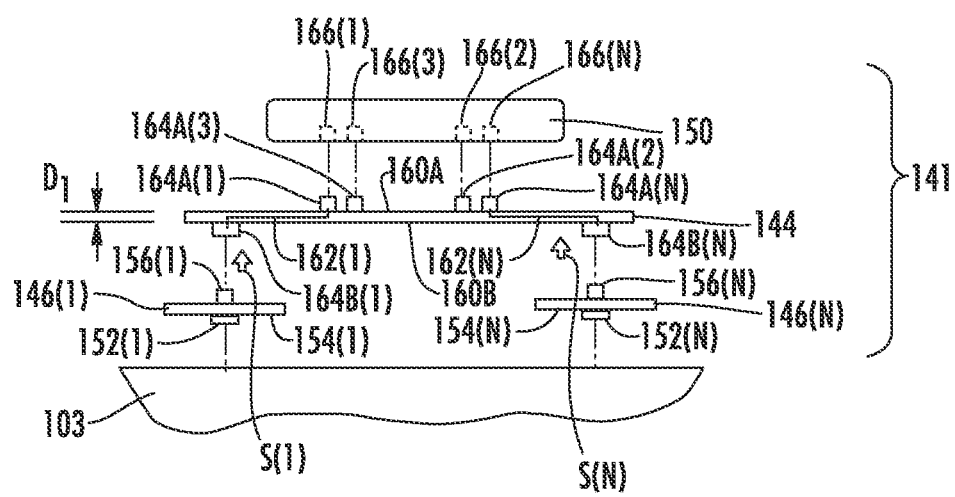
FIG. 2B is a schematic diagram of a connective relationship of the patient, the biometric sensors, the bridge connector, and the control device of FIG. 1, according to one embodiment described herein.

The bridge connector 144 physically supports and enables the control device 150 to receive the output signals S(1)-S(N) transmitted from the biometric sensors 146(1)-146(N). In this regard, FIG. 2B is a schematic diagram of a connective relationship of the patient 103, the biometric sensors 146(1)-146(N), the bridge connector 144, and the control device 150 of FIG. 1. The biometric sensors 146(1)-146(N) are brought into contact with the patient 103 of FIG. 2A. Specifically, an electrolytic portion 152(1)-152(N) respectively of the biometric sensors 146(1)-146(N) contacts the patient 103 to efficiently detect the health condition of the patient. The electrolytic portion 152(1)152(N) may be, for example, a hydrogel. The biometric sensors 146(1)-146(N) also respectively include a bonding agent 154(1)-154(N), for example an adhesive or cohesive substance, to secure the biometric sensors 146(1)-146(N) to the patient 103 while the output signals S(1)-S(N) indicating a health condition of the patient 103 are being generated by the biometric sensors 146(1)-146(N). When the biometric sensors 146(1)-146(N) need to be replaced, then biometric sensors 146(1)-146(N) may be pulled away from the patient 103 with an adequate pulling force applied to the biometric sensors 146(1)-146(N) to overcome the strength of the bonding agent 154(1)-154(N). The biometric sensors 146(1)-146(N) further include a conductive portion 156(1)-156(N) which may form a mechanical connector, for example a male snap fastener. The conductive portion 156(1)-156(N) may comprise a material (e.g. silver/silver chloride) which may efficiently form an electrical connection to the electrolytic portion 152(1)-152(N) for predictable and stable transfer of the output signals S(1)-S(N) indicative of the health condition of the patient 103. In this manner, the biometric sensors 146(1)-146(N) are removably coupled to patient 103 and generate the output signals S(1)-S(N) indicative of the health of the patient 103. In addition, the conductive portions 156(1)-156(N) serve as a foundation or physical support to hold the bridge connector 144 and the control device 150 stationary or substantially stationary to the patient 103.

With continued reference to FIG. 2B, the bridge connector 144 forms a removable attachment with the conductive portion 156(1)-156(N) of the biometric sensor 146(1)-146(N). The bridge connector 144 comprises a flexible planar body 158 including a first surface 160A and a second surface 160B opposite the first surface 160A. The first surface 160A and the second surface 160B are separated by a thickness D1 of the flexible planar body 158. The thickness D1 may be in a range from one-hundred microns to five (5) millimeters to avoid bulkiness which may be uncomfortable for the patient 103. The data ports 164B(1)-164B(N) on the second surface 160B of the bridge connector 144 include fasteners (discussed later) which may be removably coupled to the conductive portion of the biometric sensors 146(1)-146(N). The removable coupling enables inoperable ones of the biometric sensors 146(1)-146(N) to be removed from the bridge connector 144 so that they may be replaced with operational ones when the bridge connector 144 is used again. In this manner, the bridge connector 144 and the biometric sensors 146(1)-146(N) form a robust foundation or physical support to hold the control device 150.

The bridge connector 144 conforms to a shape of the patient 103 to provide comfort and efficacy. In this regard, the bridge connector 144 includes an elastic modulus of elasticity in a range from a half a megapascal to eight (8) megapascals. This modulus of elasticity enables the bridge connector 144 to provide adequate flexibility to conform to a body of the patient 103 for comfort and to maintain contact between the biometric sensors 146(1)-146(N) and the bridge connector 144 when the shape of the patient 103 is not flat in the portion where the biometric sensors 146(1)-146(N) contact. The bridge connector 144 provides adequate rigidity to support the control device 150 in stationary location relative to the patient 103 when the patient 103 dynamically moves. In this manner of constructing the bridge connector 144 with optimal rigidity, the bridge connector 144 provides comfort and efficacy.

The bridge connector 144 also forms a pathway for the output signals S(1)-S(N) generated at the biometric sensors 146(1)-146(N) to travel to the data ports 164A(1)-164A(N) at the first surface 160A of the bridge connector 144. In this regard, the flexible planar body 158 includes at least one signal pathway 162(1)-162(N) interconnecting data ports 164A(1)-164A(N) at the first surface 160A to the data ports 164B(1)-164B(N) at the second surface 160B according to a predetermined relationship. In this manner, the output signals S(1)-S(N) generated at the biometric sensors 146(1)-146(N) may be received at the data ports 164B(1)-164B(N) at the second surface 160B from the biometric sensors 146(1)-146(N) and travel to the data ports 164A(1)-164A(N) at the first side 160A of the bridge connector 144 to be made available to the control device 150. In this manner, the bridge connector 144 may provide connectivity between the biometric sensors 146(1)-146(N) and the control device 150.

The control device 150 forms a removable attachment with the data ports 164A(1)-164A(N) at the first surface 160A of the flexible planar body 158 of the bridge connector 144. The control device 150 includes device ports 166(1)-

166(N) which form a removable attachment with the data ports 164A(1)-164A(N) via a mechanical interference fit or mechanical friction. The data ports 164A(1)-164A(N) and the device ports 166(1)-166(N) are also electrically conductive enabling the output signals S(1)-S(N) to be received by the device ports 166(1)-166(N) of the control device 150 from the data ports 164A(1)-164A(N). In this manner, the control device 150 may receive the output signals S(1)-S(N) from the biometric sensors 146(1)-146(N) and be supported by the bridge connector 144 and the biometric sensors 146(1)-146(N).

Figure 3A:
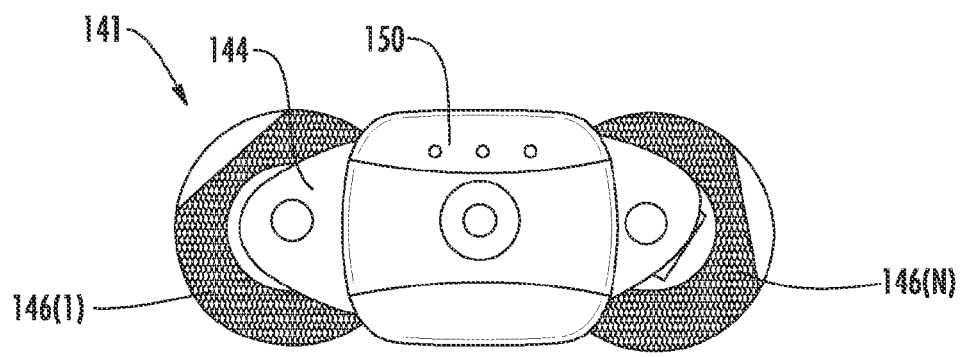
FIG. 3A through 3C are a top view, top perspective view, and top perspective exploded view, respectively, of the body sensor including the control device, the bridge connector, and at least one biometric sensor of FIG. 1, according to one embodiment described herein.
Figure 3B:
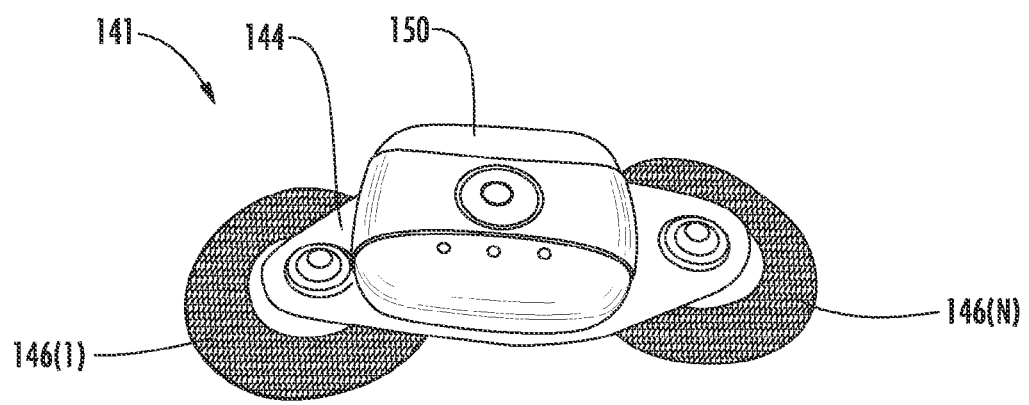
Figure 3C:
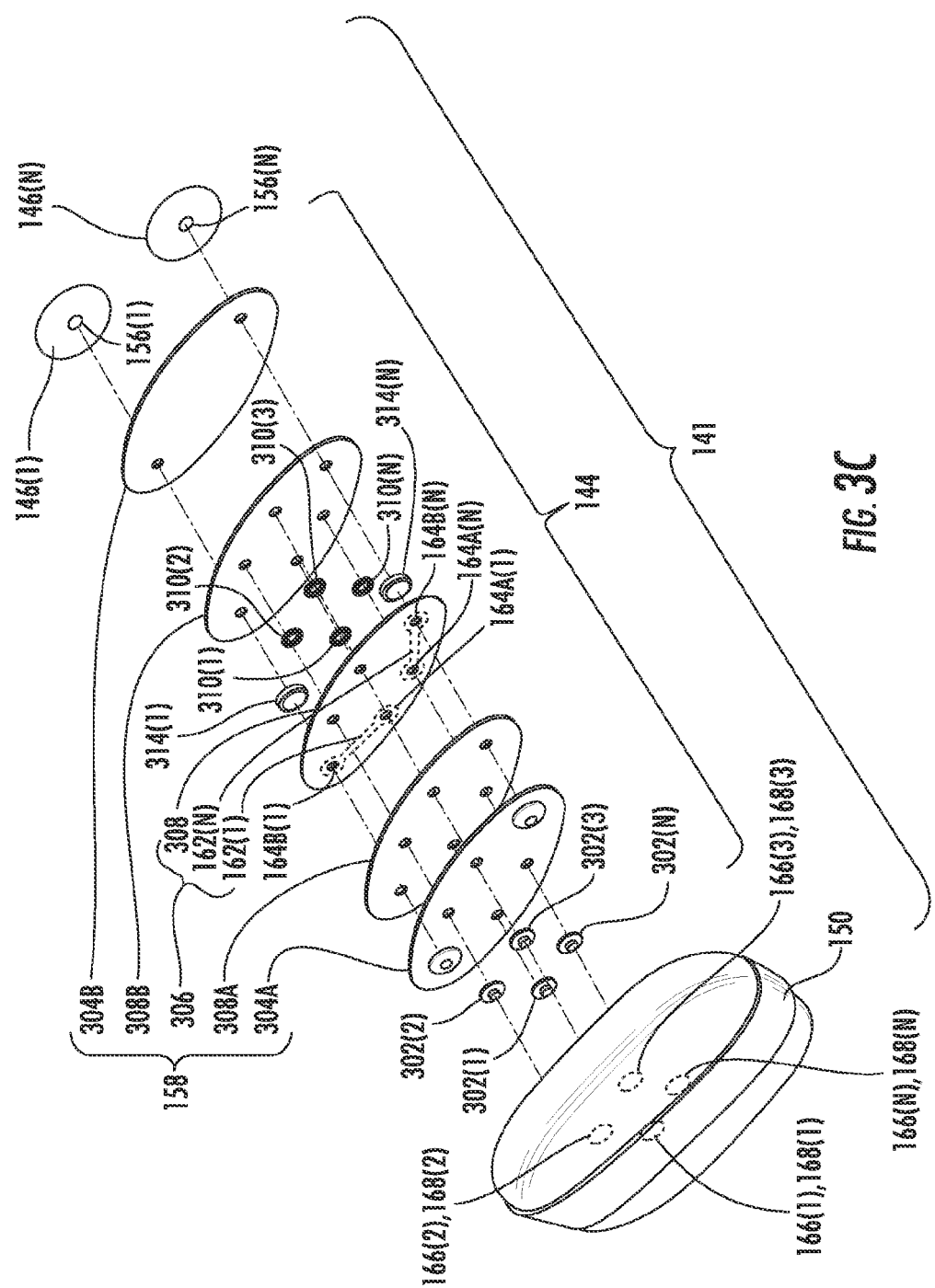

Now that the body sensor 141 has been introduced, details of the various components are now discussed. In this regard, FIG. 3A through 3C are a top view, top perspective view, and top perspective exploded view, respectively, of the body sensor 141 including the control device 150, the bridge connector 144, and the biometric sensors 146(1)-146(N) of FIG. 1. Each of these components are now discussed sequentially.

As discussed briefly earlier, the control device 150 may collect, analyze, store, and/or transmit the output signals S(1)-S(N) indicating a health condition of the patient 103 to the mobile device 135 and/or the network 145 (FIG. 1). The control device 150 is supported by the patient 103 through the biometric sensors 146(1)-146(N) and the bridge connector 144. The control device 150 is also able to receive the output signals S(1)-S(N) at the device ports 166(1)-166(N) of the control device 150 via the signal pathways 162(1)-162(N) of the bridge connector 144. In order to receive the output signals S(1)-S(N) and be physically supported by the biometric sensors 146(1)-146(N) and the bridge connector 144, the control device 150 includes the device ports 166 (1)-166(N). The device ports 166(1)-166(N) may include plugs 168(1)-168(N) (e.g., female snap fasteners) to form the removable attachment with the data ports 164A(1)-164A (N) of the bridge connector 144.

Figure 4A:
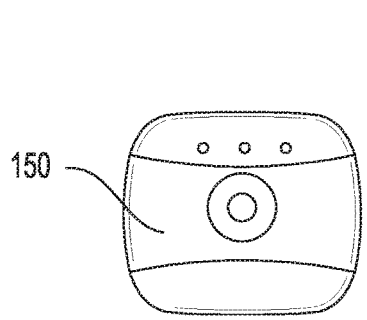
FIGS. 4A and 4B are a top view and a bottom view, respectively, of the control device of FIG. 1, according to one embodiment described herein.
Figure 4B:
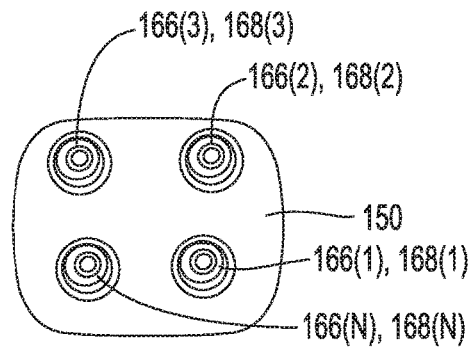

FIGS. 4A and 4B are a top view and a bottom view, respectively, of the control device 150 of FIG. 1. At the bottom of the control device 150, the device ports 166(1)-166(N) are depicted as including the plugs 168(1)-168(N)) to form the removable attachment with the data ports 164A(1)-164A(N) of the bridge connector 144. The quantity of the device ports 166(1)-166(N) may be dependent upon the quantity of the biometric sensors 146(1)-146(N). In this manner, the control device 150 may be configured to support various numbers of the biometric sensors 146(1)-146(N).

Figure 4C:
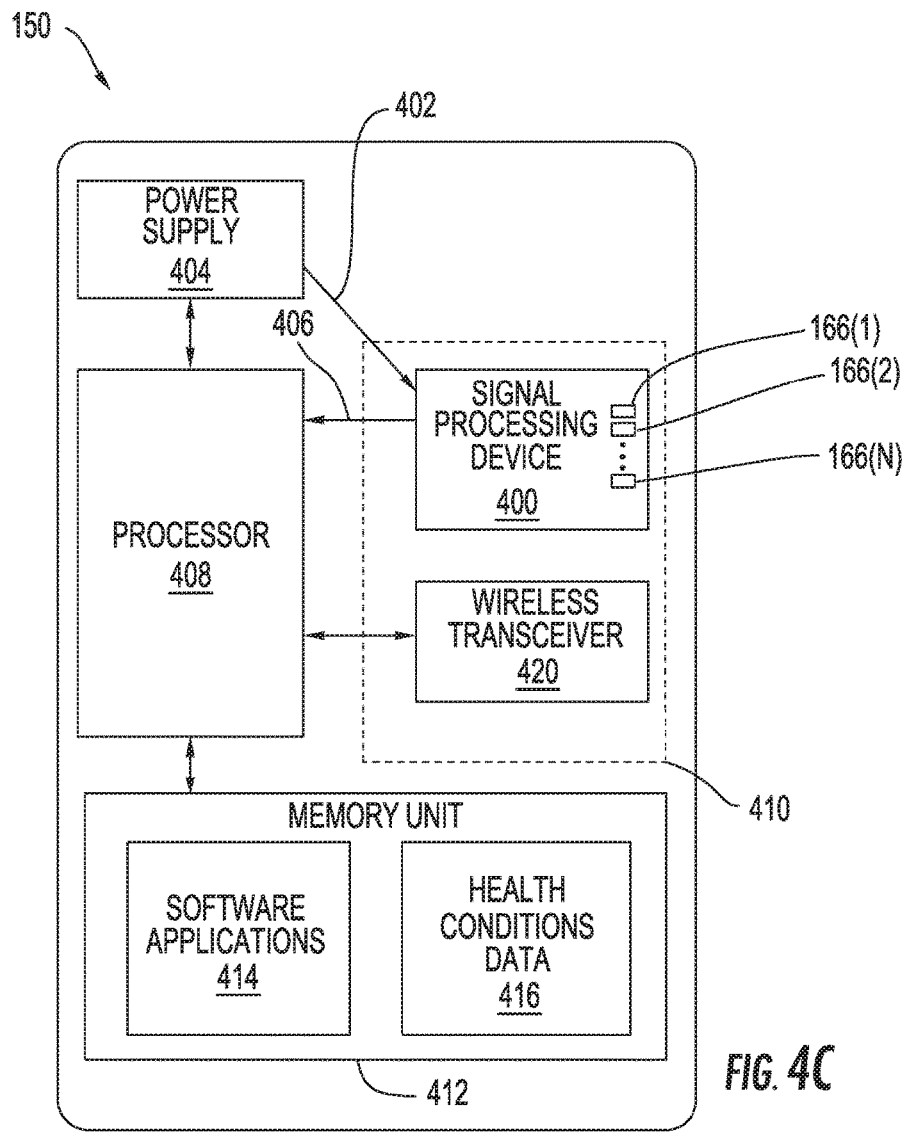
FIG. 4C is a schematic of the components of the control device of FIG. 1, according to one embodiment described herein.

FIG. 4C is a schematic diagram of the components of the control device 150 of FIG. 1, according to one embodiment of the present disclosure. In general, the control device 150 can be a computing device that can be used with other wireless or wired electronic devices. In one example, the control device 150 is able to wirelessly communicate with a similarly configured mobile device 135 and/or the network 145 (FIG. 1). During operation of the control device 150 when the biometric sensors 146(1)-146(N) generate the output signals S(1)-S(N) indicative of the health of the patient 103, the control device 150 may receive the output signals S(1)-S(N) from the biometric sensors 146(1)-146(N) via the bridge connector 144. The control device 150 may perform several operations using the output signals S(1)-S (N), including for example, data analysis, data storage, and data transmittal to the similarly configured mobile device 135 and/or the network 145. In this manner, the control device 150 may communicate the health condition of the patient 103 to the care providers 101 and/or the care provider environment 105.

An example of the control device 150 may include, but is not limited to a BodyGuardian® Remote Monitoring System available from Preventice Technologies, Inc. of Rochester, Minn. or other similar device. The control device 150 may include a power source 404, a memory unit 412, the processor 408, and input/output (I/O) devices 410. These electrical components are now discussed sequentially. In this regard, the control device 150 may be battery-operated from the power source 404, although the control device 150 may at one time or another receive power from a wired connection to a wall outlet, wireless charger or other similar devices without deviating from the basic scope of the disclosure provided herein. The power source 404 may supply power to the memory unit 412, the processor 408, and the I/O devices 410. Further, the power source 404 may be able to provide voltages to the biometric sensors 146(1)-146(N) of opposite polarity (or one positive voltage and one reference voltage) through the bridge connector 144. In other embodiments or other operational modes involving the power source 404, the biometric sensors 146(1)-146(N) may transmit the output signals S(1)-S(N) to the control device 150 in a passive manner, wherein the passive manner involves transmitting the output signals S(1)-S(N) to the control device 150 without the biometric sensors 146(1)-146(N) consuming power from the power source 404. Specifically, the biometric sensors 146(1)-146(N) may detect the tiny electrical changes on the skin of the patient 103 that arise from the heart muscle during each heartbeat. The output signals S(1)-S(N) may be in a range from 0.1 millivolts to 10 millivolts and result from these tiny electrical changes may comprise an electrocardiogram (ECG) trace over time to be amplified and filtered using energy from the power source 404. Using these approaches, the power source 404 may be used to facilitate the operation of the control device 150 as the control device 150 is coupled to the biometric sensors 146(1)-146(N) via the bridge connector 144.

It is also contemplated that in some embodiments that at least a portion of the energy from the power source 404 may be used in combination with the bridge connector 144 and the biometric sensors 146(1)-146(N) to detect respiration from the patient 103. In this regard, a bioimpedance signal may be generated using energy from the power source 404 and may travel sequentially from the control device 150, to the signal pathways 162(1), 162(N) of the bridge connector 144, to the biometric sensors 146(1)-146(N), and then to the skin of the patient 103. The bioimpedance signal may be, for example, approximately one-hundred microamperes with about a fifty kilohertz frequency. The bridge connector 144 and the power source 404 may be configured to support this approach to detect respiration in combination or apart from measuring the ECG trace.

Next, the memory unit 412 of the control device 150 contains data and instructions to facilitate the operation of the control device 150. In this regard, the memory unit 412 may be in communication with the processor 408 and include one or more software applications 414 that, when executed by the processor 408 may facilitate the operation of the control device 150. The memory unit 412 may also include storage capacity for stored health condition data 416 which may be sent to the memory unit 412 by the processor 408 and retrieved as needed by the processor 408 for analysis or transmittal to the mobile device 135 and/or the network 145 (FIG. 1). The stored health condition data 416 may include any type of information that relates to the health condition of the patient (i.e, electrocardiogram data over time), patient user data, electronic device configuration data, device control rules or other useful information, which are discussed further below. The stored health condition data 416 may include information that is delivered to and/or received from another sensor device 140 (FIG. 1). The stored health condition data 416 may reflect various data files, settings and/or parameters associated with the environment, device control rules and/or desired behavior of the control device 150. The memory unit 412 may comprise a computer-readable medium and may comprise volatile or non-volatile memory units, for example, dynamic random access memory (DRAM) units. The memory unit 412 may be any technically feasible type of hardware unit configured to store data. For example, the memory unit 412 could be a hard disk, a random access memory (RAM) module, a flash memory unit, or a combination of different hardware units configured to store data. In this manner, the memory unit 412 contains data and instructions needed for the operation of the control device 150.

The processor 408 of the control device 150 coordinates the activities of the memory unit 412, and I/O devices 410. The processor 408 may be a hardware unit or combination of hardware units capable of executing software applications and processing data. In some configurations, the processor 408 includes a central processing unit (CPU), a digital signal processor (DSP), an application-specific integrated circuit (ASIC), and/or a combination of such units. The processor 408 is generally configured to execute the one or more software applications 414 and process the stored health condition data 416, which may be each included within the memory unit 412 or in other embodiments at least partially resident in the processor 408 In this manner, the processor 408 facilitates the operation of the control device 150.

The I/O devices 410 of the control device 150 are coupled to the memory unit 412 and the processor 408, and may include devices capable of receiving input and/or devices capable of providing output. The I/O devices 410 may include a signal processing device 400 and one or more wireless transceivers 420. The signal processing device 400 includes device ports 166(1)-166(N) to communicate with the biometric sensors 146(1)-146(N) and receive the output signals S(1)-S(N) generated by the biometric sensors 146(1)-146(N). The signal processing device 400 may amplify and/or filter the output signals S(1)-S(N) from the biometric sensors 146(1)-146(N) to generate a processed signal 406 which is made available to the processor 408 which may perform further operations, for example, further data modification, analysis, storage, or transmittal. To support the operations of the signal processing device 400, the signal processing device 400 may receive electrical power 402 from the power source 404. In this manner, the control device 150 may receive the output signals S(1)-S(N) generated by the biometric sensors 146(1)-146(N) and make the output signals S(1)-S(N) available for further analysis, storage, or transmission.

Moreover, the I/O devices 410 may include the wireless transceivers 420. Each of the wireless transceivers 420 may be configured to establish one or more different types of wired or wireless communication links with other transceivers residing within other computing devices, such as the mobile device 135 (FIG. 1) or other devices in the network 145 (FIG. 1). A given transceiver within the I/O devices 410 could establish, for example, a Wi-Fi communication link, near field communication (NFC) link or a Bluetooth® communication link (e.g., BTLE, Bluetooth classic). In this manner, the I/O devices 410 of the control device 150 may make the health condition of the patient 103 available to the care providers 101 and/or the care provider environment 105.

With reference back to FIG. 3C, the bridge connector 144 may include outer structural members 304A, 304B sandwiching a flex circuit 306 and multiple bonding layers 308A, 308B (e.g., an adhesive or epoxy). The outer structural members 304A, 304B may be respectively combined with the bonding layers 308A, 308B in an adhesive-backed structure (e.g., 3M™ Thin Tan Polyethylene Foam Tape 1774T available from 3M of St. Paul, Minn.) or as separate components to be brought together during fabrication of the bridge connector 144. The flex circuit 306 includes a substrate 308 supporting the signal pathways 162(1), 162(N). The signal pathways 162(1), 162(N) may comprise a conductive material configured to efficiently transmit the output signals S(1)-S(N), for example, copper. The signal pathways 162(1)-162(N) connect and form the data ports 164A(1)-164A(N) and the data ports 164B(1)-164B(N) accessible through the substrate 308. Together the outer structural members 304A, 304B, the flex circuit 306 and the bonding layers 308A, 308B form the flexible planar body 158. The flexible planar body 158 has the modulus of elasticity mentioned earlier to provide the structural support for the control device 150 while providing comfort for the patient 103 during use by deforming to the contour of the patient 103.

The bridge connector 144 includes fasteners to provide the removable attachments with the control device 150 and the biometric sensors 146(1)-146(N) and also transmit the output signals S(1)-S(N) including the health condition from the biometric sensors 146(1)-146(N). Specifically, in one non-limiting embodiment shown in the FIG. 3C, the bridge connector 144 may include mechanical fasteners 302(1)-302(N) (e.g., male socket fasteners). The mechanical fasteners 302(1)-302(N) extend as part of the data ports 164A(1)-164A(N) to removably couple with the plugs 168(1)-168(N) (e.g., female socket fasteners) of the device ports 166(1)-166(N) of the control device 150. The bridge connector 144 may also include respective complementary mechanical fasteners 310(1)-310(N) (e.g., eyelets) supporting the mechanical fasteners 302(1)-302(N). Collectively, the mechanical fasteners 302(1)-302(N) and the complementary mechanical fasteners 310(1)-310(N) may sandwich the structural member 304A and the flex circuit 306 to provide a secure anchoring for the mechanical fasteners 302(1)-302(N) as part of the bridge connector 144. Similarly, the bridge connector 144 may include second mechanical fasteners 314(1), 314(N) (e.g., female sockets). The second mechanical fasteners 314(1), 314(N) extend as part of the data ports 164B(1)-164B(N) to removably couple with the conductive portions 156(1), 156(N) of the biometric sensors 146(1)-146(N). In this manner, the bridge connector 144 may be removably attached to the control device 150 and the biometric sensors 146(1)-146(N) and transmit output signals S(1)-S(N) therebetween.

It is noted that in one non-limiting embodiment, the second mechanical fasteners 314(1), 314(N) may be disposed between the structural member 304B and the flex circuit 306. This arrangement enables the conductive portions 156(1), 156(N) to be received within the bridge connector 144 and thereby minimizes the distance between the bridge connector 144 and the patient 103. The close proximity of the bridge connector 144 to the patient 103 facilitates a greater level of stability for the control device 150 which is secured to the patient 103 via the bridge connector 144 and the biometric sensors 146(1)-146(N).

FIGS. 5A and 5B are a top view and a bottom view, respectively, of the bridge connector 144 of FIG. 1. The bridge connector 144 is depicted with the mechanical fasteners 302(1)-302(N) at the first surface 160A of the flexible planar body 158 and the second mechanical fasteners 314(1)-314(N) at the second surface 160B of the flexible planar body 158. The bridge connector 144 may have a length L in a range from three (3) inches to eight (8) inches and a width W in a second range from one (1) inch to three (3) inches. In this manner, electrical connections for exchange of the output signals S(1)-S(N) can be accomplished with the control device 150 and the biometric sensors 146(1)-146(N).

With reference back to FIG. 3C, the body sensor 141 includes the biometric sensors 146(1)-146(N) removably coupled to the bridge connector 144. The biometric sensors 146(1)-146(N) are configured to generate the output signals S(1)-S(N) indicating a health condition of the patient 103 when electrically connected to the control device 150 and in contact with the patient 103 at one of the predetermined locations 200(1)-200(3) (FIG. 1). Each of the biometric sensors 146(1)-146(N), for example, may be a Kendall™ Electrode 530 Foam available from Medtronic, Inc. of Minneapolis, Minn. FIGS. 6A and 6B are a top view and a bottom view, respectively, of the biometric sensor 146(1) of FIG. 1. The biometric sensor 146(1) depicted includes the conductive portion 156(1) to removably couple to the second mechanical fastener 314(1) (see FIG. 3C). The biometric sensor 146(1) depicted in FIG. 6B also depicts the electrolytic portion 152(1) to contact the patient 103 and the removable bonding agent 154(1) to form the removable attachment with the patient 103.

Figure 7:
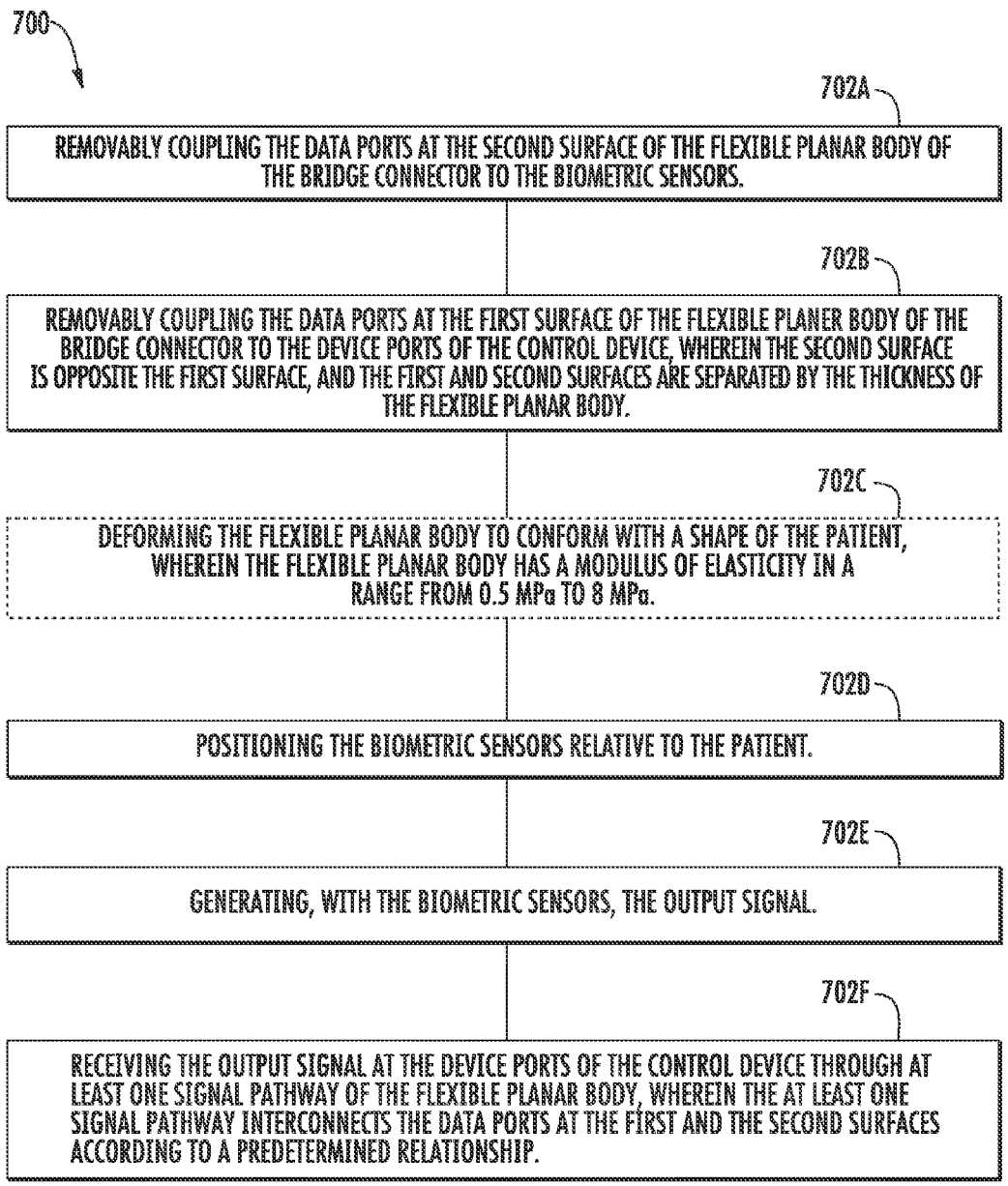
FIG. 7 is a flowchart of an exemplary method of receiving biometric data from the patient of FIG. 1, according to one embodiment described herein.

Now that the body sensor 141 has been discussed, FIG. 7 is a flowchart of an exemplary method 700 of receiving biometric data from the patient 103 of FIG. 1. The method 700 is discussed using the terminology discussed above with reference to operations 702A-702F of FIG. 7.

In this regard, the method 700 includes removably coupling the data ports 164B(1)-164B(N) at the second surface 160B of the flexible planar body 158 of the bridge connector 144 to the biometric sensors 146(1)-146(N) (operation 702A of FIG. 7). The method 700 also includes removably coupling the data ports 164A(1)-164A(N) at the first surface 160A of the flexible planar body 158 of the bridge connector 144 to the device ports 166(1)-166(N) of the control device 150, wherein the second surface 160B is opposite the first surface 160A, and the first surface 160A and the second surface 160B are separated by the thickness D1 of the flexible planar body 158 (operation 702B of FIG. 7) The method 700 may also include deforming the flexible planar body 158 to conform with a shape of the patient 103, wherein the flexible planar body 158 as a modulus of elasticity in a range from a half megapascal to eight (8) megapascals (operation 702C of FIG. 7). The method 700 also includes positioning the biometric sensors 146(1)-146(N) relative to the patient 103, wherein the biometric sensors 146(1)-146(N) may be secured to the patient 103, (operation 702D of FIG. 7). The method 700 also includes generating, with the biometric sensors 146(1)-146(N), the output signals S(1)-S(N) including biometric data measured by the biometric sensors 146(1)-146(N) from the patient 103 (operation 702E of FIG. 7). The method 700 also includes receiving the output signals S(1)-S(N) at the device ports 166(1), 166(N) of the control device 150 through the at least one signal pathway 162(1), 162(N) of the flexible planar body 158, wherein the at least one signal pathway 162(1), 162(N) interconnects the data ports 164A(1)-164A(N) at the first surface 160A and the data ports 164B(1)-164B(N) at the second surface 160B according to a predetermined relationship (operation 702F of FIG. 7). In this manner, the biometric sensors 146(1)-146(N) may be replaced when needed in the body sensor 141 with low cost.

Figure 8A:
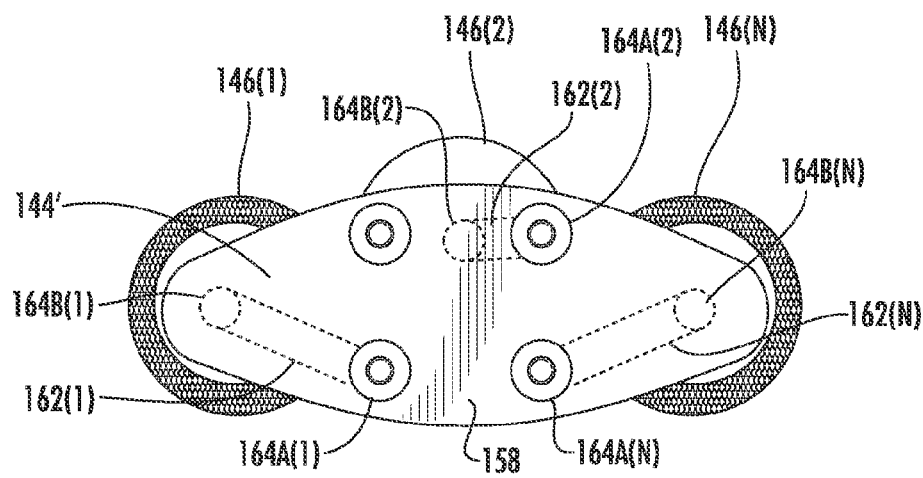
FIGS. 8A through 8C are top views, respectively, of three different embodiments of a bridge connector consistent with the computing environment of FIG. 1, according to one embodiment described herein.
Figure 8B:
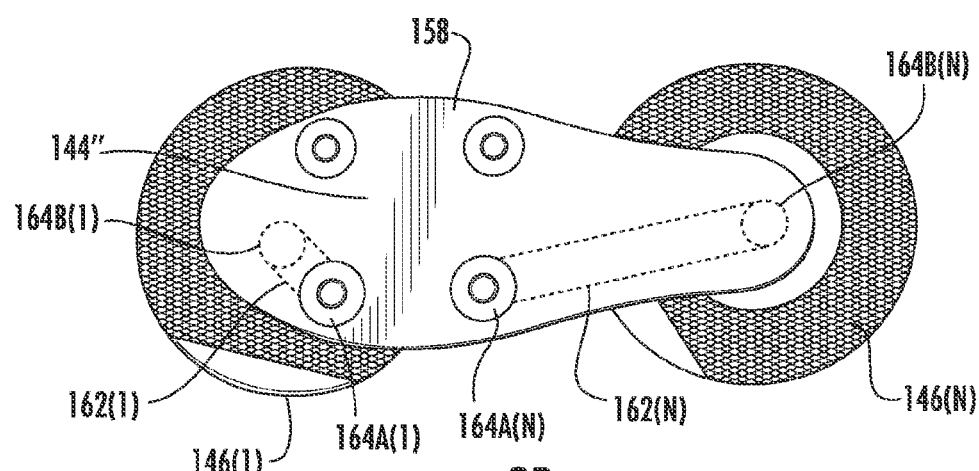
Figure 8C:
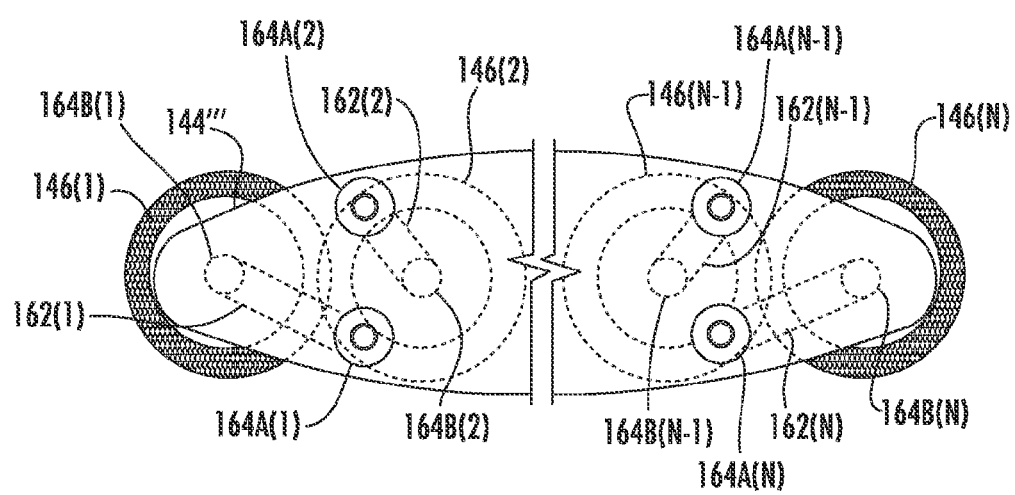

Other embodiments of the bridge connector 144 are possible. FIGS. 8A through 8C are top views, respectively, of three different embodiments of a bridge connector consistent with the computing environment 100 of FIG. 1, designated bridge connector 144', bridge connector 144", and bridge connector 144'". The bridge connector 144' facilitates the biometric sensors 146(1), 146(2), and 146(N) to be respectively connected by the signal pathways 162(1), 162(2), and 162(N) to the data ports 164A(1), 164A(2), and 164A(N). In his manner, the bridge connector 144' may support more than two biometric sensors with mechanical and/or electrical functionality. The bridge connector 144" facilitates the biometric sensors 146(1), 146(N) to be removably coupled to the electrode bridge connector 144" in an asymmetric arrangement. The bridge connector 144" facilitates at least four (4) of the biometric sensors 146(1)-146(N) to be removably coupled to the electrode bridge connector 144'". In this manner, the shape and arrangement of the bridge connector 144 may be changed to provide connectivity and support to the control device 150.

While the foregoing is directed to embodiments of the present disclosure, other and further embodiments of the disclosure may be devised without departing from the basic scope thereof.

What is claimed is:
1. A bridge connector for coupling a control device to at least one biometric sensor, comprising:
  a flexible planar body comprising:
    a first surface;
    a second surface opposite the first surface, wherein the first and second surfaces are separated by a portion of the flexible planar body;
    at least one signal pathway interconnecting a first data port from the first surface to a second data port at the second surface according to a predetermined relationship;
    a flex circuit arranged between the first and second surfaces, the flex circuit comprising both: (i) the at least one signal pathway extending within the flex circuit to carry electrical signals and (ii) a substrate configured to support the at least one signal pathway and comprising an opening; and
    a structural member arranged between the flex circuit and the second surface;
  a first and second mechanical fastener, wherein the first mechanical fastener extends through the flex circuit at the opening and couples with the second mechanical fastener; and
  wherein the first data port at the first surface is configured to be removably coupled to the control device using the first and second mechanical fasteners, the second data port at the second surface is configured to be removably coupled to the at least one biometric sensor, and the first and second data ports are configured to exchange biometric data between the data ports through the at least one signal pathway within the flex circuit and according to the predetermined relationship.

2. The bridge connector of claim 1, wherein the flexible planar body has a modulus of elasticity in a range from a half megapascal to eight (8) megapascals.

3. The bridge connector of claim 1, wherein the flexible planar body is configured to support the control device.

4. The bridge connector of claim 1, wherein the second data port at the second surface comprises a third mechanical fastener configured to removably couple with an electrocardiogram (ECG) electrode.

5. The bridge connector of claim 1, wherein the at last one signal pathway comprises a conductive material configured to exchange the biometric data in a form of an electrical signal.

6. The bridge connector of claim 1, wherein the first data port at the first surface comprises the first mechanical fastener configured to removably interface with a plug of the control device.

7. The bridge connector of claim 1, wherein the second data port at the second surface comprises a third mechanical fastener configured to removably interface with a mechanical connector of the at least one biometric sensor.

8. The bridge connector of claim 1, wherein the portion of the flexible planar body comprises a thickness in a range from one-hundred microns to five millimeters.

9. The bridge connector of claim 1, wherein the flexible planar body comprises a first plurality of data ports at the first surface, including the first data port, and a second plurality of data ports at the second surface, including the second data port, and wherein the predetermined relationship is a one-to-one relationship connecting each of the data ports at the first surface with a respective one of the data ports at the second surface.

10. The bridge connector of claim 9, wherein a location pattern of the first plurality of data ports on the first surface is different from a location pattern of the second plurality data ports on the second surface.

11. The bridge connector of claim 9, wherein two of the data ports on the second surface are separated by a distance from sixty (60) millimeters to one-hundred millimeters.

12. The bridge connector of claim 1,
wherein the second data port at the second surface comprises a third mechanical fastener configured to removably interface with a mechanical connector of the at least one biometric sensor, and wherein the third mechanical fastener originates between the structural member and the flex circuit.

13. The bridge connector of claim 12, wherein the third mechanical fastener comprises a female socket.

14. A medical device for receiving biometric data from a patient, comprising:
at least one biometric sensor for measuring the biometric data of the patient and configured to generate an output signal including the biometric data;
a control device for receiving the output signal;
a bridge connector for coupling the control device to at least one biometric sensor, comprising:
a flexible planar body comprising:
a first surface;
a second surface opposite the first surface, wherein the first and second surfaces are separated by a portion of the flexible planar body;
at least one signal pathway interconnecting a first data port from the first surface to a second data port at the second surface according to a predetermined relationship;
a flex circuit arranged between the first and second surfaces, the flex circuit comprising both: (i) the at least one signal pathway extending within the flex circuit to carry electrical signals and (ii) a substrate configured to support the at least one signal pathway and comprising an opening; and
a structural member arranged between the flex circuit and the at least one biometric sensor;
a first and second mechanical fastener, wherein the first mechanical fastener extends through the flex circuit at the opening and couples with the second mechanical fastener; and
wherein the first data port at the first surface is configured to be removably coupled to the control device using the first and second mechanical fasteners, the second data port at the second surface is configured to be removably coupled to the at least one biometric sensor, and the first and second data ports are configured to exchange the biometric data between the data ports through the at least one signal pathway within the flex circuit and according to the predetermined relationship.

15. The medical device of claim 14,
wherein the second data port at the second surface comprises a third mechanical fastener configured to removably interface with a mechanical connector of the at least one biometric sensor, and wherein the third mechanical fastener originates between the structural member and the flex circuit.

16. The medical device of claim 15, wherein the third mechanical fastener comprises a female socket.

17. A method of receiving biometric data from a patient, comprising:
measuring the biometric data of the patient using at least one biometric sensor;
generating an output signal including the biometric data, using the at least one biometric sensor;
receiving the output signal at a control device, using a bridge connector coupling the control device to the at least one biometric sensor, the bridge connector comprising:
a flexible planar body comprising:
a first surface;
a second surface opposite the first surface, wherein the first and second surfaces are separated by a portion of the flexible planar body;
at least one signal pathway interconnecting a first data port from the first surface to a second data port at the second surface according to a predetermined relationship;
a flex circuit arranged between the first and second surfaces, the flex circuit comprising both: (i) the at least one signal pathway extending within the flex circuit to carry electrical signals and (ii) a substrate configured to support the at least one signal pathway and comprising an opening; and
a structural member arranged between the flex circuit and the at least one biometric sensor; and
a first and second mechanical fastener, wherein the first mechanical fastener extends through the flex circuit at the opening and couples with the second mechanical fastener; and
wherein the first data port at the first surface is configured to be removably coupled to the control device using the first and second mechanical fasteners, the second data port at the second surface is configured to be removably coupled to the at least one biometric sensor, and the first and second data ports are configured to exchange the biometric data between the data ports through the at least one signal pathway within the flex circuit and according to the predetermined relationship.

18. The method of claim 17, wherein the flexible planar body has a modulus of elasticity in a range from a half megapascal to eight (8) megapascals.

19. The method of claim 17, wherein the flexible planar body comprises a first plurality of data ports at the first surface, including the first data port, and a second plurality of data ports at the second surface, including the second data port, and wherein the predetermined relationship is a one-to-one relationship connecting each of the data ports at the first surface with a respective one of the data ports at the second surface.

20. The method of claim 19, wherein a location pattern of the first plurality of data ports on the first surface is different from a location pattern of the second plurality data ports on the second surface.

* * * * *